US010463603B2

(12) United States Patent
Paris et al.

(10) Patent No.: US 10,463,603 B2
(45) Date of Patent: Nov. 5, 2019

(54) COSMETIC USE OF DEDIFFERENTIATED PLANT CELLS

(71) Applicant: L'OREAL, Paris (FR)

(72) Inventors: Maryline Paris, Saint Cloud (FR); Michelle Rathman Josserand, La Celle St Cloud (FR); Richard Martin, Rochecorbon (FR); Brigitte Lavaud, Paris (FR); Pascal Hilaire, Vouvray (FR)

(73) Assignee: L'OREAL, Paris (FR)

( * ) Notice: Subject to any disclaimer, the term of this patent is extended or adjusted under 35 U.S.C. 154(b) by 468 days.

(21) Appl. No.: 14/370,826

(22) PCT Filed: Jan. 4, 2013

(86) PCT No.: PCT/IB2013/050094
§ 371 (c)(1),
(2) Date: Jul. 7, 2014

(87) PCT Pub. No.: WO2013/102882
PCT Pub. Date: Jul. 11, 2013

(65) Prior Publication Data
US 2014/0356310 A1  Dec. 4, 2014

Related U.S. Application Data

(60) Provisional application No. 61/604,542, filed on Feb. 29, 2012.

(30) Foreign Application Priority Data

Jan. 5, 2012 (FR) ..................... 12 50122
Sep. 5, 2012 (FR) ..................... 12 58273

(51) Int. Cl.
A61K 8/97       (2017.01)
A61Q 5/00       (2006.01)
A61Q 19/08      (2006.01)
A61Q 19/00      (2006.01)
C12N 5/04       (2006.01)
A01H 5/02       (2018.01)
A01H 6/74       (2018.01)

(52) U.S. Cl.
CPC .............. A61K 8/97 (2013.01); A01H 5/02 (2013.01); A01H 6/749 (2018.05); A61Q 5/00 (2013.01); A61Q 5/002 (2013.01); A61Q 19/00 (2013.01); A61Q 19/08 (2013.01); C12N 5/04 (2013.01)

(58) Field of Classification Search
None
See application file for complete search history.

(56) References Cited

U.S. PATENT DOCUMENTS

| | | | |
|---|---|---|---|
| 6,586,020 B1 | 7/2003 | Breton et al. | |
| 8,609,086 B2 | 12/2013 | Steward et al. | |
| 2003/0082117 A1 | 5/2003 | Martin et al. | |
| 2005/0265953 A1 | 12/2005 | Ennamany et al. | |
| 2007/0098668 A1 | 5/2007 | Mekideche | |
| 2008/0299092 A1* | 12/2008 | Blum ................ | A61K 8/14 424/93.7 |
| 2009/0208544 A1 | 8/2009 | Ennamany et al. | |
| 2011/0097310 A1 | 4/2011 | Jang et al. | |
| 2014/0072619 A1 | 3/2014 | Blum et al. | |

FOREIGN PATENT DOCUMENTS

| | | |
|---|---|---|
| CH | 698 274 B1 | 6/2009 |
| EP | 0 909 556 A1 | 4/1999 |
| EP | 1 064 932 A1 | 1/2001 |
| EP | 1 699 423 B1 | 11/2007 |
| EP | 1 985 280 A2 | 10/2008 |
| EP | 2 266 529 A2 | 12/2010 |
| EP | 2 436 757 A2 | 4/2012 |
| EP | 2 436 758 A2 | 4/2012 |
| EP | 2 436 759 A2 | 4/2012 |
| FR | 2 890 311 A1 | 3/2007 |
| FR | 2 926 021 A1 | 7/2009 |
| FR | 2985423 A1 * | 1/2012 |
| WO | WO 01/47538 | 7/2001 |
| WO | WO 2004/082643 A2 | 9/2004 |
| WO | WO 2009/151302 A2 | 12/2009 |
| WO | WO 2010/137879 A2 | 12/2010 |
| WO | WO 2011/121051 A2 | 10/2011 |

OTHER PUBLICATIONS

Jan. 5, 2012 Written Opinion issued in French Patent Application No. 12 50122 (with translation).
Nov. 14, 2012 Search Report issued in French Patent Application No. 12 50122 (with translation).
Sep. 5, 2012 Written Opinion issued in French Patent Application No. 12 58273 (with translation).
May 24, 2013 Search Report issued in French Patent Application No. 12 58273 (with translation).
Jul. 12, 2013 Written Opinion issued in PCT/IB2013/050094.
Jul. 12, 2013 International Search Report issued in PCT/IB2013/050094.
Reid et al: "Regulation of tissue repair in plants," *Proceedings of the National Academy of Sciences*, vol. 108, No. 42; Oct. 18, 2011; pp. 17241-17242.
Anonymous: "L'Extrait—Regenerating Ultimate Elixir," XP002697377 www.gnpd.com; Database No. 1824948; Jun. 30, 2012.
Petersen et al: "Plant Cell Cultures," *Biotechnology Set, Second Edition*, Jan. 1, 2008; pp. 578-585.

* cited by examiner

Primary Examiner — Terry A McKelvey
Assistant Examiner — Catheryne Chen
(74) Attorney, Agent, or Firm — Oliff PLC

(57) ABSTRACT

The present invention relates to the cosmetic use of dedifferentiated plant cells of a plant of the *Rosa* sp. genus, or of an extract or a lyophilizate of said cells, as an active agent for caring for aged skin or aged hair. It also relates to rose dedifferentiated cells, in particular Lancôme rose dedifferentiated cells.

26 Claims, 3 Drawing Sheets

COSMETIC USE OF DEDIFFERENTIATED PLANT CELLS

Figure 1:
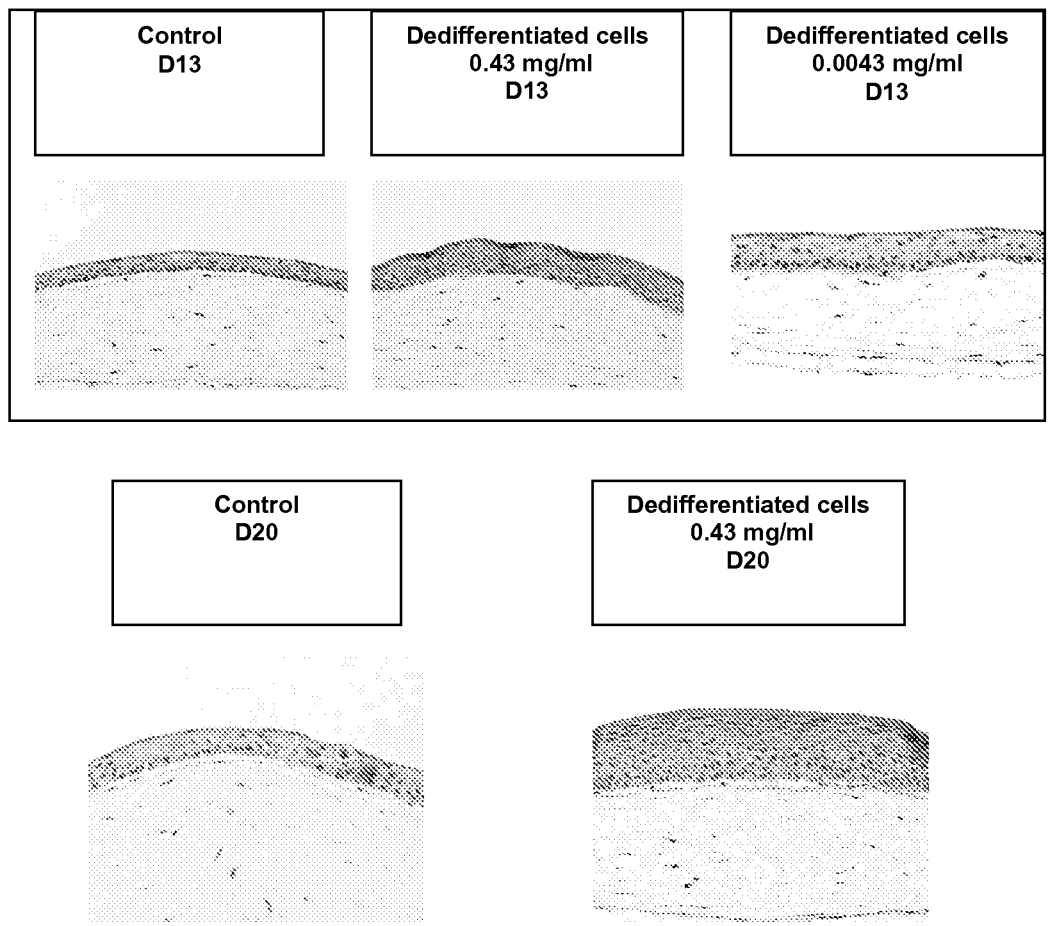

The present invention concerns the cosmetic field and relates to the use, as an active agent, of dedifferentiated plant cells of *Rosa* sp. for esthetic care of the skin and the hair.

The present invention also relates to a cell line of dedifferentiated plant cells derived from the Lancôme rosebush which are capable and effective for restoring the regenerative capacity of the skin.

In particular, the present invention relates to a cell line of dedifferentiated plant cells derived from a rosebush of the Lancôme variety, which are capable and effective for restoring the regenerative capacity of a model of reconstructed skin with low regenerative potential, and on the self-renewal capacity of a reservoir of dermal stem cells, SKPs, derived from human skin biopsies (scalp and foreskin).

The skin is a tissue which continually self-renews throughout the life of an individual. This renewal is maintained by keratinocytes which reside in the basal layer of the epidermis. This population of cells comprises, on the one hand, stem cells, which are rare cells characterized by a very substantial long-term expansion potential and also a self-renewal capacity, and, on the other hand, cells called progenitors which actively multiply and possibly differentiate while migrating to the horny layer.

With regard to hair follicles, it is known that interaction of the epithelial compartment and the dermal compartment is essential for morphogenesis and regrowth of the hair, and also for maintaining the follicle cycle. The maintaining of the functionality of these two compartments depends on the presence and on the activity of various stem cell reservoirs. A first reservoir of epithelial stem cells has been identified in a region called the "bulge" in rodents (Cotsarelis et al., Cell, 1990, 61:1329). Since this first discovery, other reservoirs of keratinocyte stem cells have been identified and, in humans, it appears that several reservoirs, which are more or less active, are nested in the outer root sheath (ORS) of the hair follicle (Rochat et al., Cell, 1994, 76:1063; Commo et al., Differentiation, 2000, 66:157; Jaks et al., Nature Genetics, 2008, 40:1291).

As regards the dermal compartment, cells called SKPs (skin-derived precursors), housed in the dermal papilla and the connective tissue sheath, have been identified as being multipotent cells involved in hair growth induction and in skin repair in mice (Biernaskie et al., Cell Stem Cell, 2009, 5:310). Several teams have demonstrated the presence of SKPs in human tissues and in particular in the dermal papilla of hair follicles (Toma et al., Stem Cells, 2005, 23:727; Hunt et al., Stem Cells, 2008, 26:163).

Aging of the cutaneous compartments is revealed, in particular, by a considerable modification of the epidermal surface, shade and surface heterogeneities (loss of the smooth appearance), a loss of elasticity, the appearance of wrinkles, a slowing down of repair/healing following injuries, a thinned epidermis, and/or loss and/or whitening of the hair, a reduced hair density, etc.

All these visible changes in the skin and the hair indicate a modification of the regenerative capacity of the cutaneous compartments. They also suggest that the essential biological functions ensuring homoeostasis and the renewal of these tissues are compromised with age.

The existing data suggest that, with age, the number of regenerative cells of the epidermis does not decrease (Giangreco et al., Aging Cell, 2008, 7:250), but that their functionality appears to be greatly affected by modifications of their microenvironment controlling the regenerative capacity of the basal layer. Thus, the decrease in the quality of the skin linked to age appears to be linked to a modified regenerative capacity of these cells. Among the key components of the microenvironment of cells, mention may be made of the intercellular interactions, the physical constraints of the basal compartment, and the paracrine factors secreted by the surrounding cells and by the resident cells of the dermal compartment.

Equally, the loss in terms of number and/or quality of the hair that is linked to alopecia or else to chronological aging suggests a modified regenerative capacity. Indeed, it has been demonstrated that the follicles of alopecia scalps shrink in length and have fewer proliferating keratinocytes in comparison with nonalopecic scalps (Ashrafussaman et al., Acta Histochem Cytochem, 2010, 43:9). Furthermore, recent studies suggest that a deficiency in the conversion of epithelial stem cells into progenitor cells plays an important role in androgenic alopecia (Garza et al., J Clin Invest, 2010). In the dermal compartment, the cells derived from the dermal papilla of alopecic scalps proliferate less rapidly in vitro and appear to be affected by premature aging compared with cells derived from nonalopecic scalps (Bahta et al., J Invest Dermatol, 2008, 128:1088) and a decrease, with age, in the number of SKPs has been observed in human tissues (Gago et al., Stem Cells, 2009, 27:1164). All these observations suggest a modification of the regenerative capacity of the compartments of the hair follicle in connection with alopecia and/or chronological aging.

Thus, in order to find solutions to counteract the modifications of the skin and the hair linked to aging, particular attention should be paid to the regenerative cells, or even to the stem cells of the skin and hair.

Dedifferentiated plant cells have arisen from the studies by Haberland in 1902. Over the past 40 years, plant cell cultures have been used for the production of metabolites of interest or for the multiplication of plants that are exactly the same (somatic embryogenesis). This plant biotechnology is based on the concept of cell totipotency: "any plant cell is capable of dedifferentiating and regenerating another individual identical to that from which it is derived". A dedifferentiated plant cell is a plant cell originating from an organ (leave, stem, root, petal, etc) which has been placed in culture, and which again takes its dedifferentiated form, i.e. it loses its leaf, stem, root or petal specificity, and again becomes possibly capable of generating the whole plant.

An undifferentiated plant cell is the equivalent of a real plant stem cell, derived from meristematic plant cells, and not having an organ-specific biological past.

WO 2009/151302 and KR 2009-0118877 describe antiaging or antioxidant compositions containing undifferentiated plant cells derived from the cambium of *Panax ginseng* or from a plant of the *Taxus* genus.

EP 1 985 280 describes the use of dedifferentiated plant cells derived from a plant of the family Rosaceae, and in particular from the apple tree *Malus domestica*, for protecting the stem cells of the skin faced with various intrinsic and extrinsic stresses, and in particular for treating damage to the skin or the hair linked to age.

EP 1 699 423 describes the use of a lyophilisate of dedifferentiated plant cells, derived from a halophilic plant, for rejuvenating the appearance of the skin.

DE-A-102 009 027 361 and EP 2 266 529 describe the use of dedifferentiated plant cells in particular derived from a plant of the *Malus* genus, for treating keratin hair fibers, and in particular protecting them against UV radiation, or for treating aged skin.

EP 0 909 556 describes the use of an extract of a plant of the family Rosaceae, in particular of a rose, optionally obtained from undifferentiated plant cells, as a bradykinin antagonist for the treatment of various conditions, in particular skin conditions.

WO2011121051 describes a preparation derived from a culture of dedifferentiated, non-elicited cells of the argania tree, the use thereof for treating skin aging, inflammation and scarring, and the production thereof.

WO200482643 describes a cosmetic composition containing Olibanum, *Boswelia* or *Negundo* dedifferentiated, elicited plant cells and exhibiting an energizing effect.

EP2436759 describes an undifferentiated cell line derived from a cambium of the family Solanaceae and exhibiting an anti-aging effect.

EP2436758 describes an undifferentiated cell line derived from a cambium of the family Ginkgoaceae and exhibiting a reinforced antioxidant effect.

EP2436757 describes an undifferentiated cell line derive from a cambium of the family Asteraceae and exhibiting a reinforced anti-inflammatory effect.

WO2010137879 describes an undifferentiated cell line derived from a cambium of the family Salicaceae and exhibiting a reinforced anti-inflammatory effect.

EP1064932 describes the use of dedifferentiated cells exhibiting an anti-odor effect.

EP1244464 describes the use of extracts of dedifferentiated cells of the *Leontopodium* genus as an anti-ultraviolet screening agent.

To the knowledge of the applicant, no document therefore makes reference to obtaining a rosebush dedifferentiated cell line exhibiting the specific cosmetic properties described in the present description.

There is a need to identify technical solutions for improving the functionality and/or the activity of regenerative cells, including skin or hair stem cells, for preserving skin quality and function and also hair quality, density and shape, throughout the lifetime of an individual, and in particular for preventing and/or treating effects on the appearance of the skin or the hair linked to age.

In particular, there is a need to provide novel active agents for counteracting the deficiencies in tissue renewal of the skin or of the hair, in particular for reducing thinning of the epidermis, improving the surface appearance of the skin, correcting wrinkles, slowing down and/or inhibiting hair loss, or slowing down and/or inhibiting whitening of the hair.

The object of the present invention is, in particular, to satisfy these needs.

According to one of its first aspects, the present invention relates to the cosmetic use of dedifferentiated plant cells of a plant of the *Rosa* sp. genus, or of an extract or a lyophilisate of said cells, as an active agent for caring for aged skin or aged hair, and in particular of a Lancôme rosebush.

Unexpectedly, the inventors have observed that rose dedifferentiated plant cells, or an extract or a lyophilisate of said cells, have proved to be particularly capable and effective for restoring, in vitro, the regenerative capacity of a model of reconstructed skin produced from a keratinocyte population depleted of epidermal stem and progenitor cells. An increase in the thickness of the epidermis and a very clear improvement in the morphological quality (organization of the basal layer, stratification and differentiation, etc) have been observed after 3 weeks of culture including 2 weeks of treatment.

It has been shown by the inventors that the rose dedifferentiated plant cells, or an extract or a lyophilisate of said cells, exert a pro-regenerating effect, at least in part, through an optimization of the communication between the epidermis and the dermis. Indeed, the inventors have observed that the treatment of reconstructed skins with a reduced regenerative potential using rose dedifferentiated plant cells of the invention, or an extract or a lyophilisate of said cells, induces the expression of numerous diffusible biological factors, and in particular of KGF (Keratinocyte Growth Factor) known for its beneficial effects on epidermal regeneration. Thus, the inventors have observed that the rose dedifferentiated plant cells, or an extract or a lyophilisate of said cells, have proved to be particularly capable and effective for inducing the skin to produce physiological factors which restore the regenerative capacity of the basal layer comprising stem cells and progenitor cells.

Still unexpectedly, the inventors have observed that rose dedifferentiated plant cells, or an extract or a lyophilisate of said cells, have proved to be particularly effective for stimulating the self-renewal capacity of a reservoir of dermal stem cells, SKPs, derived from human biopsies (scalp and foreskin). Thus, an increase of approximately 65% in the self-renewal capacity of SKPs after treatment for 10 days could be observed. This active agent evaluation study makes it possible to conclude that the self-renewal capacity of SKPs in vitro can be positively affected by a treatment with rose dedifferentiated cells or an extract or a lyophilisate of said cells.

Surprisingly, the inventors have also shown that rose dedifferentiated plant cells, or an extract or a lyophilisate of said cells, have an ability to stimulate or restore the regenerative capacity of the skin, whereas compounds described in the prior art as having skin-regenerating properties, such as retinol, have not caused any detectable effect under the same test conditions.

The stimulation of the self-renewal of the regenerative cells of the skin, of the dermis and of the hair follicle allows an improvement in their functionality with benefits for the skin and for the hair. This stimulatory effect on this reservoir of dermal stem cells advantageously makes it possible to preserve, or even restore, the biological functions of these cells with cosmetic benefits for the skin and for the hair.

For the purposes of the invention, the term "skin" is intended to mean the entire cutaneous surface of an individual, including the scalp.

For the purposes of the invention, the term "hair" is intended to mean an assembly comprising the hair shaft and the hair follicle.

According to yet another embodiment, the present invention relates to the cosmetic use of dedifferentiated plant cells from a plant of the *Rosa* sp. genus, in particular of the Lancôme rosebush, or of an extract or a lyophilisate of said cells, as an active agent for treating and/or preventing an esthetic defect subsequent to a deficiency in the tissue renewal of aged skin or of aged hair.

For the purposes of the present invention, the term "preventing" means reducing the risk of manifestation of the phenomenon under consideration.

According to yet another embodiment, the present invention is directed toward counteracting the deficiencies in tissue renewal of aged skin or hair, in particular for reducing thinning of the epidermis or of the skin, improving the surface appearance of the skin, correcting wrinkles, slowing down and/or inhibiting hair loss, or slowing down and/or inhibiting whitening of the hair.

According to yet another of its objects, the present invention relates to a cosmetic composition comprising, as active agent, at least one dedifferentiated plant cell of a plant of the *Rosa* sp. genus, or an extract or a lyophilisate of said cells, said dedifferentiated plant cells being obtained by placing cells of a plant of the *Rosa* sp. genus in culture in a culture medium comprising at least $NH_4NO_3$; $KNO_3$; $CaCl_2.2H_2O$; $MgSO_4$; $KH_2PO_4$; $MnSO_4.4H_2O$; $ZnSO_4.7H_2O$; $Na_2MoO_4.2H_2O$; $CuSO_4.5H_2O$; $FeSO_4.7H_2O$; myo-inositol; nicotinic acid; pyridoxine HCl; thiamine HCl; and sucrose; and optionally kinetin, KI, $Na_2EDTA.2H_2O$, and/or naphthaleneacetic acid.

According to another of its subjects, the present invention relates to a cosmetic composition comprising, as active agent, at least one dedifferentiated plant cell derived from a Lancôme rosebush, or an extract or a lyophilisate of said cell.

According to another of its subjects, the present invention relates to a cosmetic method for caring for aged skin or aged hair, comprising at least one step consisting in administering, as active agent, at least one dedifferentiated plant cell of a plant of the *Rosa* sp. genus, or an extract or a lyophilisate of said cell, to an individual in need thereof.

According to a further embodiment, the dedifferentiated plant cells of a plant of the *Rosa* sp. genus, or an extract or a lyophilisate of said cells, in accordance with the invention, can be administered orally or topically. According to one preferred embodiment, the invention is used topically.

According to one advantage of the invention, an active agent of the invention makes it possible to stimulate the dermal cells of the hair follicle.

Advantageously again, an active agent of the invention makes it possible to stimulate the self-renewal of the stem or progenitor cells of the skin or of the hair, and to improve their functionality with a view to exerting a beneficial effect regarding the skin and the hair, in particular aged skin and hair.

According to another advantage, an active agent of the invention makes it possible to preserve, or even restore, the biological functions of the reservoir of stem cells of the skin and of the hair.

Dedifferentiated Plant Cells and Method for Obtaining Same

For the purposes of the invention, the term "dedifferentiated plant cell" is intended to mean any cell strain derived from organs of a rosebush of the *Rosa* sp. genus and obtained by means of specific in vitro culture conditions, which no longer exhibits any specialization character and which is capable, under the effect of an induction, of any differentiation in accordance with its genome and of generating, by itself, a whole plant of the plant from which it originates. Such cells are capable of living by themselves and not in a dependency relationship with other cells.

The dedifferentiated plant cells are distinct from the undifferentiated plant cells which naturally exist in plants.

For the purposes of the invention, the term "dedifferentiated plant cell" is intended to mean a strain obtained by in vitro or in vivo culture, derived from organs of a Lancôme rosebush, capable of differentiating, and/or of acquiring new characteristics of a specialized cell, under the effect of an induction into any cell type (totipotent) or into several cell types (pluripotent), in particular embryogenic or meristematic cells.

Under normal conditions, plant cells express approximately 20% of their genome, the remaining 80% being expressed only in response to particular environmental conditions. The in vitro culturing of these cells under particular culture conditions makes it possible to "reprogram" the cells and thus to access a part of this genome not expressed in the whole plant. Certain compounds, difficult to obtain by extraction from plants, become more accessible in cell cultures.

Thus, advantageously, the dedifferentiated plant cells of the invention make it possible to access novel compounds not present in the whole plant, or to significantly increase the expression of molecules that are known but rare in the whole plant.

Dedifferentiated plant cells of the invention can be obtained from any plant of the *Rosa* sp. genus. These cells can be obtained from plant material derived from whole plants or from plant parts, such as the leaves, stems, flowers, petals, sepals or roots cultivated in vivo or in vitro.

The term "in vivo culture" is intended to mean any culture of conventional type, that is to say in soil in the open air or in a greenhouse, or else out of soil.

The term "in vitro culture" is intended to mean all the techniques known to those skilled in the art for artificially obtaining a plant or a plant part. The selection pressure imposed by the physicochemical conditions during the growth of plant cells in vitro makes it possible to obtain a standardized plant material that is available throughout the year, in contrast with plants cultivated in vivo.

Preferentially, according to the invention, a plant derived from in vivo culture is used.

Preferably, dedifferentiated plant cells of the invention are obtained from at least one leaf of a plant of the *Rosa* sp. genus.

The *Rosa* genus comprises more than 200 species, among which mention may be made of *Rosa alba, Rosa alpina, Rosa canina, Rosa cinnamonea, Rosa gallica, Rosa repens, Rosa rubrifolia, Rosa rubiginosa, Rosa sempervirens, Rosa spinosissima, Rosa stylosa, Rosa tomentosa*, or *Rosa villosa*.

More preferably, the dedifferentiated plant cells of the invention are obtained from a Lancôme rosebush, and more particularly from a rosebush called Lancôme delboip Rose. Such a rosebush is commercially available, for example from the company DELBARD (France).

Most preferably, the dedifferentiated plant cells according to the invention are obtained using, as starting product, leaves of a Lancôme delboip rosebush or cells derived from said leaves.

The Lancôme rosebush is a tea hybrid, the female roots of which are a hybrid obtained by crossing of the varieties Dr. Albert Schweitzer×[Michèle Meilland×Bayadère] and which has been pollinated by the variety Melmet.

Depending on the culture method chosen, and in particular depending on the culture medium chosen, it is possible to obtain, from one and the same plant, dedifferentiated plant cells having different characteristics.

According to one preferred embodiment, the dedifferentiated plant cells of the invention are obtained from plant material derived from Lancôme rosebush leaves.

According to one preferential embodiment, a culture medium suitable for obtaining dedifferentiated plant cells of the invention comprises hormones naturally present in plants.

According to one preferential embodiment, the Lancôme rosebush dedifferentiated cells are obtained by means of a method comprising the following steps:
   a) providing Lancôme rose leaves, or cells derived from said leaves,
   b) cultivating the leaves or the cells provided in step a) in the presence of at least one plant hormone, so as to generate dedifferentiated cells, and c) recovering the dedifferentiated cells obtained at the end of step b).

In step a), the "leaves" encompass whole leaves and leaf fragments. In step a), the cells derived from leaves can be obtained according to any technique well known to those skilled in the art.

Preferentially, the leaves or cells derived from leaves are provided in axenic form (freed of any biological contaminant).

In step b) of the method, the leaves or the cells derived from leaves are cultivated in a suitable culture medium, which comprises at least one plant hormone. In certain embodiments, said culture medium comprises a plurality of plant hormones, for example two or three plant hormones.

Preferentially, the culture medium comprises at least one hormone, and entirely preferably at least one phytohormone. The phytohormones encompass in particular auxins, cytokinins and gibberellins.

The auxins which are quite particularly suitable for the invention are in the main IAA (indole-3-acetic acid), IBA (indolebutyric acid), phenylacetic acid and NAA (naphthaleneacetic acid). Preferentially, 2,4-D (2,4-dichlorophenoxyacetic acid) is excluded from the auxins which are suitable for the invention, since it is an unnatural compound.

The cytokinins, involved in cell elongation, which are quite particularly suitable for the invention are most importantly kinetin (N-(furan-2-ylmethyl)-7H-purin-6-amine; CAS Ref n° 525-79-1), zeatin (2-méthyl-4-(7H-purin-6-ylamino)but-2-en-1-ol; CAS Ref n° 1637-39-4) and benzyl adenine (N-benzyl-7H-purin-6-amine; CAS Ref n° 1214-39-7).

The gibberellins form a family of plant hormones or phytohormones, which encompass more than a hundred or so compounds, these compounds being listed via their order number GA1, GA2, . . . / . . . GA126. The various gibberellins are very close to one another from the structural point of view. The gibberellins that are particularly suitable for the invention are essentially from roots and comprise a very large number of derivatives, the most important of which are gibberelic acid, also called gibberellin A3, and gibberellins A1 and A12.

In step b) of the method, the plant hormone(s) is (are) preferentially chosen from indole-3-acetic acid, indolebutyric acid, phenylacetic acid, naphthaleneacetic acid, kinetin, zeatin, benzyl adenine, gibberelic acid, and gibberellins A1, A3 and GA3. In step b), a combination of plant hormones, for example a combination of naphthaleneacetic acid and kinetin, can be used.

According to one embodiment, a culture medium that is suitable for obtaining dedifferentiated plant cells of the invention comprises at least $NH_4NO_3$; $KNO_3$; $CaCl_2.2H_2O$; $MgSO_4$; $KH_2PO_4$; $MnSO_4.4H_2O$; $ZnSO_4.7H_2O$; $Na_2MoO_4.2H_2O$; $CuSO_4.5H_2O$; $FeSO_4.7H_2O$; myo-inositol; nicotinic acid; pyridoxine HCl; thiamine HCl; and sucrose; and optionally KI; kinetin, $Na_2EDTA.2H_2O$, and/or naphthaleneacetic acid.

According to another embodiment, a culture medium that is suitable for obtaining dedifferentiated plant cells of the invention comprises at least $NH_4NO_3$; $KNO_3$; $CaCl_2.2H_2O$; $MgSO_4$; $KH_2PO_4$; $MnSO_4.4H_2O$; $ZnSO_4.7H_2O$; KI; $Na_2MoO_4.2H_2O$; $CuSO_4.5H_2O$; $Na_2EDTA.2H_2O$; $FeSO_4.7H_2O$; myo-inositol; nicotinic acid; pyridoxine HCl; thiamine HCl; naphthaleneacetic acid; kinetin; and sucrose.

Advantageously, a culture medium can comprise from 1200 to 2000 mg/l of $NH_4NO_3$; from 1500 to 2100 mg/l of $KNO_3$; from 300 to 500 mg/l of $CaCl_2.2H_2O$; from 150 to 200 mg/l of $MgSO_4$; from 153 to 187 mg/l of $KH_2PO_4$; from 10 to 30 mg/l of $MnSO_4.4H_2O$; from 5 to 10 mg/l of $ZnSO_4.7H_2O$; from 0 to 0.91 mg/l of KI; from 0 to 0.30 mg/l of $Na_2MoO_4.2H_2O$; from 0.01 to 0.05 mg/l of $CuSO_4.5H_2O$; from 10.5 to 50 mg/l of $Na_2EDTA.2H_2O$; from 10 to 30 mg/l of $FeSO_4.7H_2O$; from 70 to 150 mg/l of myo-inositol; from 0.3 to 0.6 mg/l of nicotinic acid; from 0.4 to 0.6 mg/l of pyridoxine; from 0.08 to 0.15 mg/l of thiamine; from 0 to 11 mg/l of naphthaleneacetic acid; from 0 to 0.066 mg/l of kinetin; and from 10 to 35 g/l of sucrose.

The culturing in step b) is advantageously carried out at a temperature ranging from 24 to 30° C., and preferably from 26 to 27° C.

The culturing in step b) is advantageously carried out in an atmosphere comprising a partial $O_2$ pressure of approximately 10%.

The method is preferentially carried out batchwise for 6 to 10 days.

The method can be carried out according to a fed batch fermentation or continuous fermentation technique.

After culturing in a suitable medium, the dedifferentiated plant cells of the invention are harvested in step c), for example by filtration, and can be lyophilized or be subjected to an extraction process.

According to one particular embodiment, the culturing step b) is carried out for a period of from 6 to 14 days, and preferentially from 6 to 10 days.

The present invention also relates to dedifferentiated cells of Lancôme rosebush, in particular to these dedifferentiated cells of Lancôme delboip rosebush, said dedifferentiated cells being obtained by means of the method detailed in the present description, including in the examples.

The inventors have shown that the method according to the invention makes it possible to obtain cell lines of Lancôme rosebush dedifferentiated cells, it being possible for the cells in the cell lines to be cultivated in the form of dedifferentiated cells over a very long period of time, or even indefinitely, without detectable modification of their morphology, and without detectable modification of their properties, in particular without detectable modification of their skin-regenerating properties.

The cell lines of Lancôme rosebush dedifferentiated cells according to the invention are characterized in particular by the following characteristics:
- the size of the rare isolated cells (<5%) does not exceed a diameter of between 10 and 30 μm,
- the very predominant cell aggregates have a diameter of between 50 and 300 μm,
- the cells have a globular morphology and are white in color,
- compared with other rosebush cell lines, the culture comprises very little cell debris, and the aggregates are quite homogeneous with an average diameter of about one hundred microns,
- the Lancôme rosebush dedifferentiated cell cultures do not exhibit any particular odor.

The invention also relates to the cell line isolated by the applicant and deposited according to the Treaty of Budapest on Jul. 4, 2012, under the reference 2-6307 with the Deutsche Sammlung von Mikroorganismen und Zellkulturen (DSMZ) [German Collection of Microorganisms and Cell Cultures].

Advantageously, according to the present invention, fresh or lyophilized dedifferentiated plant cells, or extracts thereof, or those formulated in compositions which stabilize them, can be used.

The lyophilized dedifferentiated plant cells can be re-extracted with water. The lyophilization of the dedifferentiated plant cells advantageously makes it possible to separate the active agents from the biopolymer fillers, such as the cell wall polysaccharides.

In certain embodiments, the dedifferentiated cells are lyophilized, and then resuspended. The cell debris that may be present in the suspension obtained is removed, for example by passing through a syringe and then centrifugation. The suspension with the cell debris removed can be used as active agent derived from dedifferentiated plant cells according to the invention.

According to one embodiment of the invention, an extract of dedifferentiated plant cells can be used. The invention necessarily relates to the active extracts of the dedifferentiated plant cells from the viewpoint of the effects to be obtained on aged skin and aged hair. The activity of an extract of the invention can, in particular, be evaluated by means of the various experimental protocols detailed in the examples indicated hereinafter.

Any extraction method known to those skilled in the art can be used to prepare an extract of dedifferentiated plant cells according to the invention.

As an extract that is suitable for the invention, mention may be made of aqueous extracts, alcoholic extracts or extracts using an organic solvent.

The term "aqueous solvent" is intended to mean any solvent constituted totally or partly of water. Mention may thus be made of water itself, aqueous-alcoholic solvents in any proportion or else solvents constituted of water and a compound such as propylene glycol in any proportion. Among the alcoholic solvents, mention may in particular be made of ethanol.

An extraction method which is suitable for the invention may comprise a first step of grinding the dedifferentiated plant cells, for example in a cold aqueous solution, then a second step of removing the particles in suspension from the aqueous solution resulting from the first step, and a third step of sterilizing the aqueous solution resulting from the second step. This aqueous solution corresponds to an extract.

The extract obtained can then be lyophilized by any conventional lyophilization methods. A powder is thus obtained, which can be used directly or else mixed into an appropriate solvent before use.

The dedifferentiated plant cells of the invention can also be used in the form of a lyophilisate. Such a lyophilisate can be obtained by any lyophilization method known to those skilled in the art.

In principle, lyophilization consists in removing the water from a liquid, pasty or solid product, by means of the combined action of cold and vacuum. When water is heated in the solid state at very low pressure, the water sublimates, i.e. it goes directly from the solid state to the gaseous state. The water vapor (or vapor of any other solvent) leaves the product and it is captured by freezing using a condenser, or trap. This technique makes it possible to preserve both the volume and the appearance of the product treated. It can take place naturally (drying on a mountain) or more rapidly, in a freeze-dryer.

Lyophilization generally comprises three steps: freezing, sublimation and secondary drying.

Freezing consists in very rapidly bringing a substance to a temperature of between $-20°$ C. and $-80°$ C., so as to block the water in the form of ice in the situation where it was in the liquid state; lysis of the cells is thus avoided.

Sublimation consists in eliminating the "free" water. Under a vacuum of about 100 μbar, but which can vary greatly from one product to another, heat is supplied to the product; the ice undergoes sublimation. Depending on the product and the production needs, the temperature can be varied during the cycle. The water vapour is captured by a "trap" or "condenser" and the dehydration of the product will proceed continuously. When the majority of the water has undergone sublimation, the product has lost approximately 80% to 90% of its water.

Drying consists in removing the captive water from the product. In this step, the vacuum is high, up to about 5 μbar. At this stage, the product is 95% dry.

For example, after recovery of the cells from the culture medium by filtration on a cloth with a controlled porosity (approximately 80 μm), the cells are frozen at low temperature, preferably from $-20°$ C. to $-80°$ C., under conditions which make it possible to avoid the formation of large ice crystals capable of damaging them. The frozen cells are then subjected to a step of sublimation of the ice in a vacuum ranging from 5 to 500 μbar, and preferably a vacuum of 100 μbar.

As indicated above, the freeze-dried plant cells of the invention can be rehydrated before use.

Surprisingly, the applicant has shown that the effects, on skin regeneration, of the dedifferentiated Lancôme rosebush cells according to the invention, or of an extract or a lyophilisate of said cells, are significantly different than those observed with nondedifferentiated rosebush cells, or an extract or a lyophilisate of said cells.

In particular, the applicant has shown that the effects, on skin regeneration, of the dedifferentiated Lancôme rosebush cells, or of an extract or a lyophilisate of said cells, are different than those observed with nondedifferentiated Lancôme rosebush cells, or an extract or a lyophilisate of said cells.

Also surprisingly, the applicant has shown that the Lancôme rosebush dedifferentiated cells, or an extract or a lyophilisate of said cells, exhibit a particular effect on the profile of gene expression by human skin cells. The inventors have shown that the Lancôme rosebush dedifferentiated cells, or an extract or a lyophilisate of said cells, exhibit a specific effect on gene expression by human skin cells, in comparison with the effect on gene expression by skin cells which is induced by dedifferentiated cells of a rosebush of other varieties (or an extract or a lyophilisate of said cells), and also by nondedifferentiated Lancôme rosebush cells (or an extract or a lyophilisate of said cells).

Aged Skin and Signs of Skin Aging

The term "aged skin" is intended to mean a general esthetic condition of the skin resulting from chronological aging and/or photo-induced aging.

More particularly, the present invention is directed toward preventing and/or reducing and/or treating signs of skin aging.

The expression "signs of skin aging" is intended to mean any of the modifications of the external appearance of the skin due to aging which is of chronological and/or photo-induced origin.

By way of example of this modification considered in the invention, mention may be made of a surface which is not very homogeneous and is less smooth, an epidermis which is thinned and/or less effective in terms of barrier function (which repairs less quickly following attacks), wrinkles and fine lines, withered skin, a lack of elasticity and/or of tonicity of the skin, thinning of the dermis and/or degradation of the collagen fibers, which leads to the appearance of flaccid and wrinkled skin.

Said expression is also intended to mean all the internal modifications of the skin which are not systematically reflected by a modified external appearance, for instance all the internal degradations of the skin, and more particularly the degradation of the elastin fibers, or elastic fibers, subsequent to exposure to ultraviolet radiation.

In particular, the signs of skin aging that are targeted by the invention are chosen from thinning of the skin, a loss of firmness, a loss of elasticity, a loss of density or a loss of tonicity of the skin, dryness of the skin, a alteration of the surface appearance of the skin, the appearance of a marked microrelief of the skin, the appearance of roughness, the formation and/or presence of fine lines and/or of wrinkles, a modification of the radiance of the skin complexion, a wizened appearance of the skin, a modification of the odor of the skin, sagging of the skin, or withering of the skin.

Preferably, the signs of skin aging that are targeted by the invention are chosen from thinning of the skin, the appearance of a marked microrelief of the skin, the formation and/or the presence of fine lines and/or wrinkles, sagging of the skin and withering of the skin.

More preferably, the signs of skin aging that are targeted by the invention are chosen from the appearance of a marked microrelief of the skin, the formation and/or the presence of fine lines and/or wrinkles, sagging of the skin and withering of the skin.

Hair Anti-Aging

The modifications of the quality of the hair which appear with age consist in particular of a change in appearance of the fiber (thin, lifeless, weak hair with no hold), with no radiance, and/or graying, more readily brittle, and also a loss of hair density.

The present invention is thus directed toward restoring/maintaining a good hair density, and/or improving the quality of the head of hair and/or of the hair fibers, and in particular aged hair. More particularly, the dedifferentiated plant cells of the invention, or an extract or a lyophilisate of said cells, make it possible to prevent a loss of hair density and to protect, reinforce or improve the quality of aged hair in order to impart a young and dense appearance to hair.

According to one embodiment, the dedifferentiated plant cells of the invention, or an extract or a lyophilisate of said cells, are particularly suitable for preventing and/or limiting the formation of thin, lifeless, brittle, weak hair with no hold, no radiance and/or which is graying.

According to another embodiment, the dedifferentiated plant cells of the invention, or an extract or a lyophilisate of said cells, are also suitable for improving the quality of keratin fibers, in particular by promoting the growth of shiny and/or thick and/or lively hair.

According to another embodiment, the dedifferentiated plant cells of the invention or an extract or a lyophilisate of said cells, are of use for preventing and/or treating split ends, for improving the softness felt by the consumer, or for improving the vigor of the fiber, the volume of the head of hair and the sheen thereof.

According to another embodiment, the dedifferentiated plant cells of the invention, or an extract or a lyophilisate of said cells, are suitable for preventing and/or treating partial or total loss of hair fibers, and more particularly of the hair. Still preferably, the invention is suitable for preventing and/or treating alopecia.

Alopecia is more particularly reflected by a partial or total loss of the hair in an individual. Individuals who suffer an alopecic state can, in particular, be the victim of diffuse alopecia, for instance androgenetic alopecia or seborrheic alopecia or else common baldness, due to an excess of androgens (male hormones). In this type of alopecia, it is noted, mainly in men, that, in the area constituting the top of the head (vertex), the hair production cycles sometimes stop prematurely, a phenomenon which is not observed for the areas of the circumference of the head, and in particular of the nape of the neck.

According to another embodiment, the dedifferentiated plant cells, or an extract or a lyophilisate of said cells, are quite particularly suitable for preventing and/or treating whitening of the hair, and preferably canities.

Canities corresponds to the natural whitening of the hair, which appears with age or following an oxidative stress. More particularly, canities is linked to a specific and gradual increased scarcity of the melanocytes of the hair, affecting both the melanocytes of the hair bulb and the melanocyte precursor cells.

Advantageously, the present invention makes it possible to prevent, limit and/or reduce the whitening or greying of the hair and/or of body hairs. In particular, the dedifferentiated plant cells, or an extract or a lyophilisate of said cells, can be of use for preventing, limiting and/or stopping the development and/or the progression of canities.

The dedifferentiated plant cells, or an extract or a lyophilisate of said cells, can also be used for preventing and/or limiting and/or slowing down the increase in the number of white hairs in the total head of hair, and/or reducing or maintaining the percentage of white hairs relative to the total number of hairs.

According to one particular embodiment, the invention is also directed toward maintaining the natural pigmentation of the hair.

Galenic Formulation

Dedifferentiated plant cells of the invention, or an extract or a lyophilisate of said cells, can be formulated in any compositions suitable for cosmetic or pharmaceutical use.

A composition according to the invention comprises a physiologically or pharmaceutically acceptable medium.

After culturing in a suitable medium, the dedifferentiated plant cells of the invention are harvested by filtration, and can be lyophilized or be extracted or placed in solution.

Advantageously, the dedifferentiated plant cells of the invention, or an extract or a lyophilisate of said cells, can be formulated or placed in solution in water or a water-soluble organic solvent, or in mixture thereof.

A water-soluble organic solvent suitable for the invention can be chosen from $C_2$ to $C_8$, preferably $C_3$ to $C_6$, hydrocarbon-based compounds comprising from 2 to 6 hydroxyl groups, preferably from 3 to 5 hydroxyl groups, and mixtures thereof.

Among the water-soluble organic solvents suitable for the invention, mention may in particular be made of glycols containing from 2 to 8 carbon atoms, such as ethylene glycol, propylene glycol or 1,3-propanediol, 1,3-butylene glycol, dipropylene glycol, glycerol, sorbitol, and mixtures thereof. Preferably, quite particularly suitable for the invention is propylene glycol or 1,3-propanediol.

A water-soluble organic solvent can constitute from 20% to 100% by weight of the composition containing it, preferably from 30% to 90%, preferably from 40% to 80%, and more preferably from 50% to 70% by weight of the composition containing it.

A water suitable for the invention may be a spring and/or mineral water, chosen in particular from Vittel water, waters from the Vichy basin and la Roche Posay water.

The water can constitute from 20% to 100% by weight of the composition containing it, preferably from 30% to 90%, preferably from 40% to 80%, and more preferably from 50% to 70% by weight of the composition containing it. Advantageously, the water constitutes up to 50% by weight of the composition containing it.

According to one embodiment, a preparation containing dedifferentiated plant cells of the invention, or an extract or a lyophilisate of said cells, can comprise at least one hydrophilic gelling agent. Such an agent makes it possible to avoid or reduce settling out of the cells.

A hydrophilic gelling agent suitable for the invention can be chosen from polysaccharide polymers and mixtures thereof.

For the purposes of the present invention, the term "polysaccharide polymer" is intended to denote any carbohydrate molecule formed by the linking of a large number of elementary sugars, for instance xylose, glucose, galactose, rhamnose, mannose, fucose and arabinose, and their respective acids. The polysaccharide polymers in accordance with the invention are preferably chosen from polymers having molecular weights ranging from 10 to 250 kDa. As polysaccharide polymers suitable for the invention, mention may in particular be made of pectin; guar gum; cellulose; dextrin; maltodextrin; starch; tara gum; locust bean gum; inulin; acacia gum; gum arabic; fucose-rich polymers, such as Fucogel; carrageenans; konjac gum; xanthan gum; dextran; chitosan; gum tragacanth; ghatti gum; karaya gum; tamarin gum; agar-agar; alginate; gellan gum; and mixtures thereof. Use is preferably made of xanthan gum, locust bean gum, guar gum, gellan gum, agar-agar, alginate, and mixtures thereof.

According to one preferred embodiment, a preparation containing dedifferentiated plant cells of the invention, or an extract or a lyophilisate of said cells, can comprise a xanthan gum.

A gelling agent may be present in a proportion ranging from 0.01% to 10% by weight and preferably from 0.1% to 5% by weight of polysaccharide polymer(s), relative to the total weight of the composition.

According to another embodiment, a preparation containing dedifferentiated plant cells of the invention, or an extract or a lyophilisate of said cells, can comprise at least one sugar.

A sugar suitable for the invention may be a $C_4$ to $C_6$ monosaccharide, and may in particular be chosen from inositol, mannitol, glucose, sucrose, trehalose, maltose, xylitol and fructose, and mixtures thereof.

The sugar content in a composition of the invention may range from 1% to 80% by weight, for example from 5% to 75% by weight and in particular from 10% to 70% by weight, relative to the total weight of the composition.

According to one preferred embodiment, the dedifferentiated plant cells of the invention, or an extract or a lyophilisate of said cells, can be formulated in the presence of water, of 1,3-propanediol and/or of xanthan gum.

Whatever the formulation used for employing the dedifferentiated plant cells of Rosa sp., or an extract or a lyophilisate of said cells, they are necessarily employed in an effective amount.

An effective amount is the amount required to obtain a desired effect from the viewpoint of an indication under consideration by the invention.

This amount depends of course on various parameters, such as the desired effect, or the age, the weight, the height or the type of the individual to be treated, and on the route of administration, and can therefore vary to a large extent. This amount can be determined by any method known to those skilled in the art.

To give an order of magnitude, the dedifferentiated plant cells of the invention, or an extract or a lyophilisate of said cells, can be used in an amount representing from 0.01% to 30% by weight of dry matter relative to the total weight of the composition containing them, and preferentially in an amount representing from 0.1% to 50% by weight of dry matter relative to the total weight of the composition.

Dedifferentiated plant cells of Rosa sp. of the invention, or an extract or a lyophilisate of said cells, can be formulated in any cosmetic compositions, in particular intended to be ingested, injected or applied to the skin, the hair, the nails or the mucous membranes (oral, jugal, gingival, genital, conjunctival). Depending on the mode of administration selected, a composition of the invention may be in any of the galenic forms normally used.

For topical application to the skin, a composition may be in the form in particular of an aqueous or oily solution or of a dispersion of the lotion or serum type, of emulsions of liquid or semi-liquid consistency of the milk type, obtained by dispersion of a fatty phase in an aqueous phase (O/W), or vice versa (W/O), or of suspensions or emulsions of soft consistency, of the aqueous or anhydrous gel or cream type, or else of microcapsules or micro particles, or of vesicular dispersions of ionic and/or nonionic type. These compositions are prepared according to the usual methods.

These compositions may constitute cleansing, protective, treating or care creams for the face, the hands, the feet, the major anatomical folds or the body (for example day creams, night creams, makeup-removing creams, foundation creams or anti-sun creams), fluid foundations, makeup-removing milks, protective or care body milks, anti-sun milks, skincare lotions, gels or foam, for instance cleansing lotions, anti-sun lotions, artificial tanning lotions, bath compositions, deodorant compositions containing a bactericidal agent, aftershave gels or lotions, or hair-removing creams. These compositions can also consist of solid preparations constituting soaps or cleansing bars or be packaged in the form of an aerosol composition also comprising a pressurized propellant.

A composition intended to be applied to the hair can be in the form of aqueous, alcoholic or aqueous-alcoholic solutions, or in the form of creams, gels, emulsions or mousses, or else in the form of aerosol compositions also comprising a pressurized propellant. Such a composition can be in the form of a haircare composition, such as a shampoo, a hair setting lotion, a treating lotion, a hairstyling gel or cream, a dye (in particular oxidation dye) composition, a coloring shampoo, a restructuring lotion, a permanent-waving composition (in particular a composition for the first step of a permanent wave), an anti-hairloss gel or lotion.

For subcutaneous or intradermal administration, a composition can be in the form of an aqueous or oily lotion or in the form of a serum.

A composition suitable for ingestion can be in the form of capsules, granules, syrups or tablets.

The amounts of the various constituents of the compositions according to the invention are those conventionally used in the fields under consideration.

When a composition is an emulsion, the proportion of the fatty phase may range from 5% to 80% by weight and preferably from 5% to 50% by weight relative to the total weight of the composition. The oils, waxes, emulsifiers and coemulsifiers used in a composition in emulsion form are chosen from those conventionally used in the cosmetics field. The emulsifier and the coemulsifier may be present, in a composition, in a proportion ranging from 0.3% to 30% by weight and preferably from 0.5% to 20% by weight relative to the total weight of the composition.

When a composition is an oily solution or gel, the fatty phase may represent more than 90% of the total weight of the composition.

In a known manner, a cosmetic composition of the invention may also contain adjuvants that are customary in the cosmetics field, such as hydrophilic or lipophilic gelling agents, hydrophilic or lipophilic additives, preservatives, antioxidants, solvents, fragrances, fillers, screening agents, odor absorbers and colorants. The amounts of these various adjuvants are those conventionally used in the cosmetics field, and are, for example, from 0.01% to 10% of the total weight of the composition. Depending on their nature, these agents can be introduced into the fatty phase, into the aqueous phase and/or into lipid spherules.

As oils or waxes that may be used in the invention, mention may be made of mineral oils (liquid petroleum jelly), plant oils (liquid fraction of shea butter, sunflower oil), animal oils (perhydrosqualene), synthetic oils (purcellin oil), silicone oils or waxes (cyclomethicone) and fluoro oils (perfluoropolyethers), beeswax, carnauba wax or paraffin wax. Fatty alcohols and fatty acids (stearic acid) can be added to these oils.

As emulsifiers that can be used in the invention, mention may, for example, be made of glyceryl stearate, polysorbate 60 and the mixture of PEG-6/PEG-32/glycol stearate sold under the name Tefose$^R$ 63 by the company Gattefosse.

As solvents that can be used in the invention, mention may be made of lower alcohols, in particular ethanol and isopropanol, and propylene glycol.

As hydrophilic gelling agents that can be used in the invention, mention may be made of carboxyvinyl polymers (carbomer), acrylic copolymers such as acrylate/alkyl acrylate copolymers, polyacrylamides, polysaccharides such as hydroxypropylcellulose, natural gums, preferably xanthan, and clays, and, as lipophilic gelling agents, mention may be made of modified clays such as bentones, metal salts of fatty acids, for instance aluminum stearates and hydrophobic silica, ethylcellulose and polyethylene.

Cosmetic Method

According to another of its aspects, the present invention relates to a cosmetic method for caring for aged skin or aged hair, comprising at least one step consisting in administering, as active agent, at least one dedifferentiated plant cell of a plant of the *Rosa* sp. genus, or an extract or a lyophilisate of said cell, to an individual in need of same. Such a method can be carried out in particular by administering a cosmetic composition as defined above, according to the usual technique for use of this composition.

According to one embodiment, the invention relates to a cosmetic method for treating and/or preventing an esthetic defect subsequent to a deficiency in tissue renewal of aged skin or of aged hair in an individual in need of same, comprising at least one step of administering to said individual, as active agent, at least one dedifferentiated plant cell of a plant of the *Rosa* sp. genus, or an extract or a lyophilisate of said cell.

A method according to the invention may comprise a step consisting in observing a reduction or even the disappearance of the esthetic defects subsequent to a deficiency in tissue renewal of aged skin or of aged hair.

Advantageously, the implementation of a method of the invention makes it possible to reinforce, improve or even restore a young appearance of the skin and/or of the head of hair.

A cosmetic method according to the invention may be carried out in particular by oral or topical, preferably topical, administration of a cosmetic composition as defined above.

A method of the invention may be carried out on a daily basis for example, at a rate of, for example, a single administration per day or one administration twice a day, for example once in the morning and once in the evening.

A cosmetic method according to the invention may be carried out, for example, by daily administration of a composition formulated, for example, in the form of gels, lotions, creams, foams, gel capsules, sugar-coated tablets, emulsions, tablets, capsules or oral vials, in appropriate amount and number, depending on their form.

An effective amount of an active agent of the invention may be administered in a single dose per day or in fractional doses over the day, for example two to three times a day.

A method according to the invention may advantageously comprise a single administration.

A cosmetic method according to the invention may be carried out over a time period ranging from one week to several weeks, or even several months, this period moreover possibly being repeated after periods without treatment, for several months or even several years.

By way of example, the administration of an active agent according to the invention may be repeated, for example 2 to 3 times per day, or more, and generally over an extended period of at least 4 weeks, or even 4 to 15 weeks, with, where appropriate, one or more periods of interruption.

FIGURES

FIG. 1: represents photographs of models of reconstructed skins with low regenerative potential, in section, after treatment for 10 days in the absence (control) or in the presence of Lancôme rosebush dedifferentiated cells at 0.43 mg/ml or 0.043 mg/ml and culturing up to 13 (top photograph) or 20 (bottom photograph) days.

Figure 2:
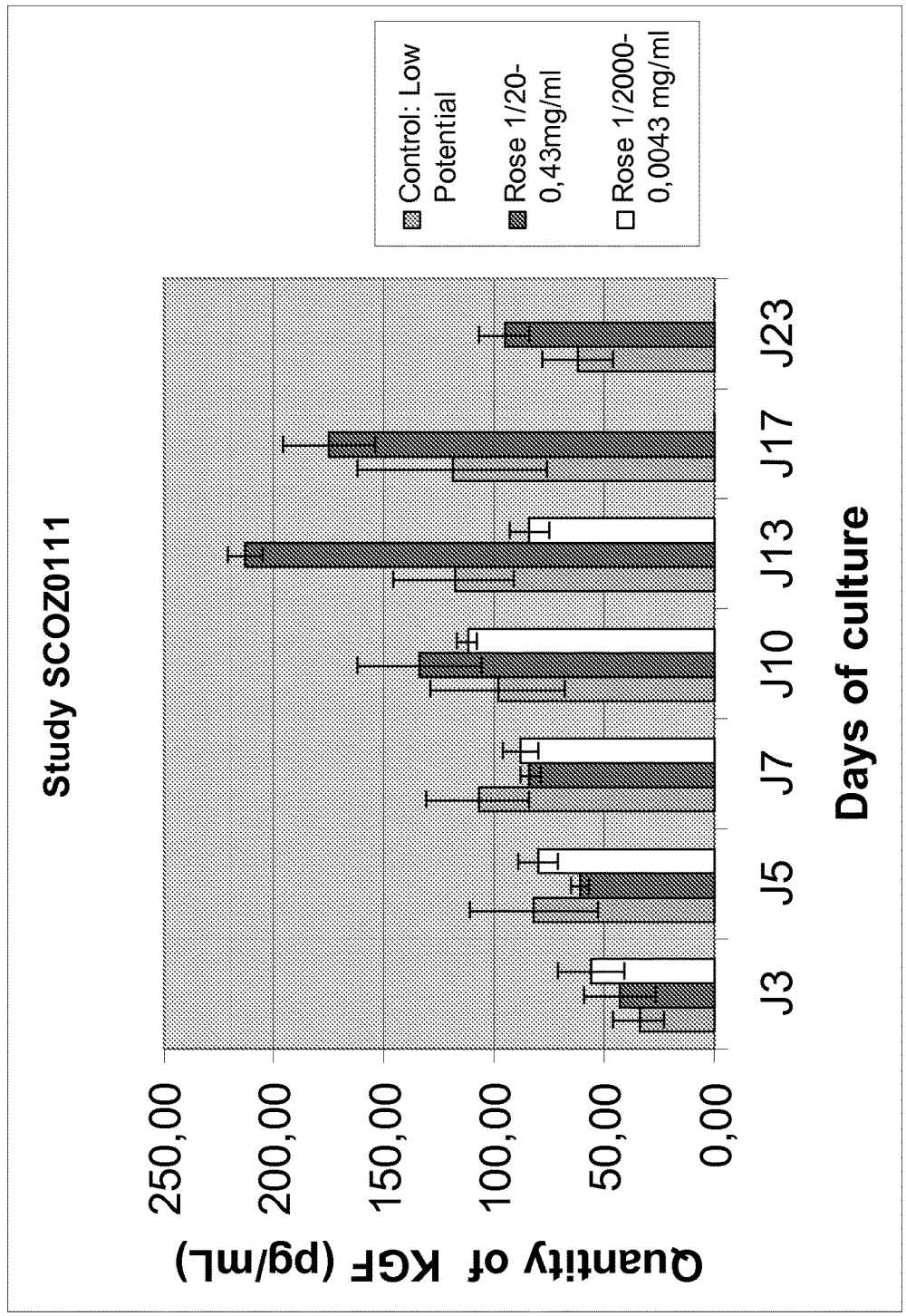

FIG. 2: represents the amount of keratinocyte growth factor (KGF) determined in the culture media of models of reconstructed skins with low regenerative potential, treated in the absence or in the presence of Lancôme rosebush dedifferentiated cells (0.43 mg/ml). The analyses were carried out on D3, D5, D7, D10, D13, D17 and D23. Light gray histogram: control. Dark gray histogram: Lancôme rosebush dedifferentiated cells at 0.43 mg/ml. White histogram: Lancôme rosebush dedifferentiated cells at 0.0043 mg/ml.

Figure 3:
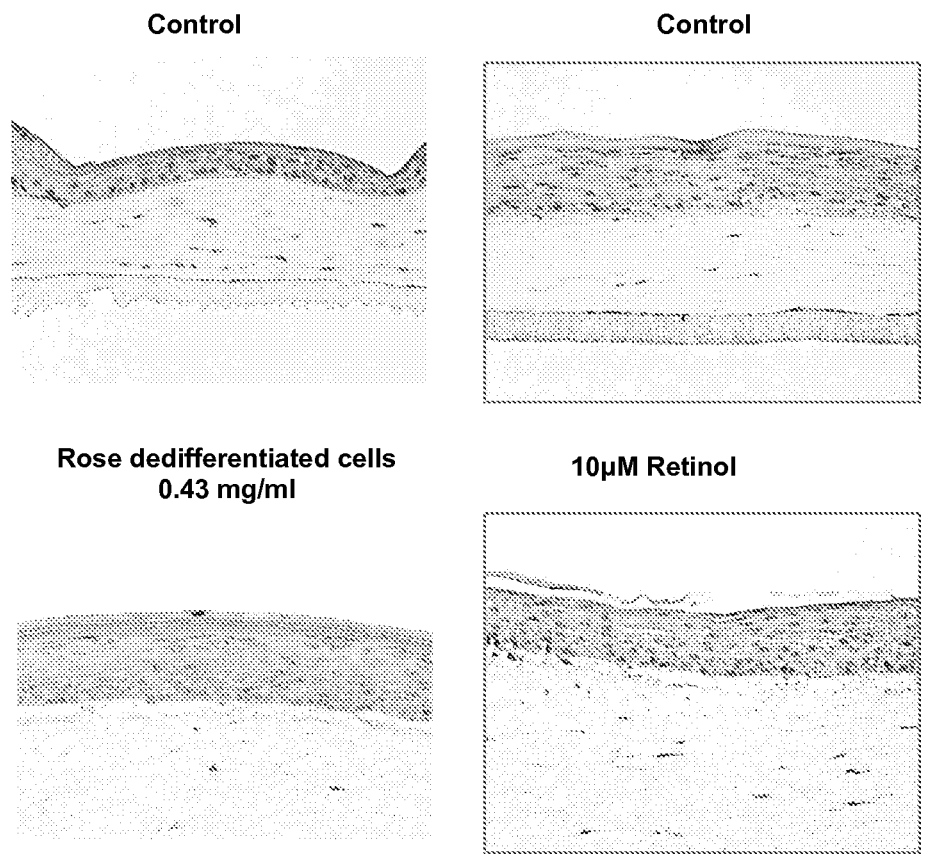

FIG. 3: represents photographs of models of reconstructed skins with low regenerative potential, in section, which are untreated (control) or treated in the presence of rosebush dedifferentiated plant cells at 0.43 mg/ml or in the presence of retinol at 10 µM.

In the description and in the examples that follow, unless otherwise indicated, the percentages are percentages by weight and the ranges of values written in the form "between . . . and . . . " include the specified lower and upper limits. The ingredients are mixed, before being formed, in the order and under conditions that are easily determined by those skilled in the art.

The examples hereinafter are presented as nonlimiting illustrations of the field of the invention.

EXAMPLES

Example 1

Culture of Rosebush (Lancôme Rose) Dedifferentiated Plant Cells Using Plant Tissue Leaves of a rosebush (Lancôme Rose) were decontaminated by means of the usual techniques of those skilled in the art, and placed on the following culture medium:

| | mg/l |
|---|---|
| MACRONUTRIENTS | |
| NH$_4$NO$_3$ | 1650 |
| KNO$_3$ | 1900 |
| CaCl$_2$•2H$_2$O (CX41) | 440 |
| MgSO$_4$ | 180.8 |
| KH$_2$PO$_4$ | 170 |
| MICRONUTRIENTS | |
| MnSO$_4$•4H$_2$O | 22.3 |
| ZnSO$_4$•7H$_2$O | 8.6 |
| KI | 0.83 |
| Na$_2$MoO$_4$•2H$_2$O | 0.25 |
| CuSO$_4$•5H$_2$O | 0.025 |
| Na$_2$ EDTA•2H$_2$O | 37.3 |
| FeSO$_4$•7H$_2$O | 27.8 |
| VITAMINS | |
| MYO-INOSITOL | 100 |
| NICOTINIC ACID | 0.5 |
| PYRIDOXINE HCl (B$_6$) | 0.5 |
| THIAMINE HCl (B$_1$) | 0.1 |
| HORMONES | |
| Naphthaleneacetic acid | 10 |
| Kinetin | 0.06 |
| CARBON SOURCE | |
| Sucrose | 30000 |

The hormones used are hormones naturally present in plants.

Following successive subculturings, dedifferentiated plant cells that can be cultivated in a fermenter and are therefore industrializable were obtained. The parameters used for the control of the culture in a bioreactor are the following:

T°: from 24° C. to 30° C., ideally 26-27° C.

Aeration: pO$_2$ 10%, regulated by the sterile air entering and/or via agitation while avoiding any shear stress on the cells.

The batchwise production lasts from 6 to 14 days. The cells are then harvested by filtration on a cloth with a porosity of 80 μm.

The Lancôme rosebush dedifferentiated cells obtained are formulated in water, in the presence of 1,3-propanediol and of xanthan gum in a proportion of 10% by weight of fresh biomass relative to the total weight of the composition.

Example 2

Demonstration of the "Pro-Regenerating" Effects of the Lancôme Rosebush Dedifferentiated Plant Cells on a Model of Reconstructed Skin with Low Regenerative Potential a—Preparation of the Models of Reconstructed Skin with Low Regenerative Potential Keratinocytes were isolated from a human skin specimen. After removal of the subcutaneous tissue with a scalpel, the skin specimen was cut into fragments and then decontaminated by means of an antibiotic-antimycotic treatment in DMEM culture medium (Life Technologies Ltd, Scotland).

In order to enable the dermis to be separated from the epidermis, the specimen was subsequently subjected to a proteolytic treatment (Dispase II)/Trypsin 0.25%) overnight at 4° C. The fragments of epidermis separated from the dermal tissue were placed in a 1× trypsin-EDTA solution for 20 minutes at 37° C. The effect of the trypsin was neutralized by adding a culture medium containing 10% of fetal calf serum (FCS). The cell suspension was homogenised and then washed in keratinocyte culture medium (keratinocyte growth medium, KGM) (KGM Bullet Kit, BioWhittaker, Clonetics Corp., San Diego, Calif., USA). The cell suspension was then placed in culture flasks pre-"coated" with collagen type I (Sigma Chemical Co Ltd, Irvine, UK). After 15 minutes, the keratinocytes which had not adhered were recovered by washing in PBS buffer. The nonadherent cells thus selected are depleted of stem and progenitor cells of the basal layer.

This subpopulation of keratinocytes was seeded, in a proportion of from 150 000 to 450 000 cells, in culture medium (N Fortunel et al (2011). Eur J Dermatol. 21(52): 12-20) onto the upper part of a dermal support placed beforehand in an insert.

The culture substrate used is a devitalized human dermis free of epidermis or a live dermis comprising fibroblasts within a collagen lattice (stretched model, production Episkin®). Medium is then added below and above each insert and this medium is renewed every two days. After 6-7 days at 37° C. in an incubator at 5% CO$_2$, the medium on the upper part of the sample was completely drawn off and the medium below the insert was replaced with the same medium mentioned below but devoid of transferrin, of triiodothyronine and of adenine. This begins the emersion phase necessary for inducing the stratification and differentiation of the epidermal compartment. The samples were cultivated for 1-3 weeks at 37° C. and 5% CO$_2$, the medium is renewed every two days.

b—Treatments with the Dedifferentiated Plant Cells

The rose dedifferentiated cells obtained in example 1 were lyophilized, then resuspended by successive passage in a syringe. The cell debris was removed by centrifugation. The resulting active agent with the cell debris removed was used in a proportion of 0.43 mg/ml and 0.043 mg/ml. The active agent was applied systemically (in the culture medium below the inserts) as soon as the dermal support was seeded with keratinocytes. The application of the active agent was renewed on days 3, 6, 8 and 10. Histological analyses:

thickness of the epidermis,
general organization,
stratification,
quality of the basal layer, etc., were carried out on day 13 and on day 20.

The control corresponds to culture medium devoid of rose dedifferentiated cells.

As shown in FIG. 1, in the presence of rose dedifferentiated cells, thickening of the epidermis was observed. Furthermore, the basal layer is more dense, the morphological quality is improved and correct differentiation, namely stratification of the living layers and a semblance of a granular layer, is observed.

These results demonstrate a restoration of the regenerative capacity of the models of reconstructed skins with low regenerative potential, following the treatments performed with dedifferentiated cells of a rosebush (Lancôme Rose) and support the use of such an ingredient for treating the skin.

Example 3

Titration of the Secretion of Keratinocyte Growth Factor (KGF) Induced by Treating a Model of Reconstructed Skin, with Low Regenerative Potential, with Lancôme Rosebush Dedifferentiated Plant Cells The culture media of the experiments described in example 2 were collected on days 3, 5, 7, 11, 13, 17 and 20. The soluble amounts of KGF secreted by the reconstructed skins and present in these media were then analysed by ELISA (Enzyme-linked immunosorbent assay) (R&D Systems, Catalog N°DKG00).

As shown in FIG. 2, an increase in secretion of KGF was observed in comparison with the control (untreated), especially on day 13 following treatments with the rose dedifferentiated cells at 0.43 mg/ml.

This growth factor is produced by the fibroblasts and it is known for its mitogenic effects on kératinocytes (Finch P W et al. Science 1989 245:752; Marchese et al. J Cell Physiol 1990 144:326). This result shows that the rose (Lancôme Rose) dedifferentiated plant cells induce secretion of diffusible factors, produced at least in part by the fibroblasts, which have a beneficial effect on epidermal regeneration. A pro-regenerating dialogue is therefore created between the dermis and the epidermis.

Example 4

Demonstration of the Beneficial Effects on the Self-Renewal of Dermal Stem Cells in Vitro Isolation of Dermal Stem Cells Derived from Human Biopsy Stem cells derived from the dermal compartment (SKPs) have the capacity to proliferate and to self-renew in the form of spheres in suspension when they are cultivated in vitro in the presence of FGF2 and EGF. They are isolated from the skin and the hair follicles according to the protocol described in the publication *Nature Protocols* (Biernaskie et al. 2006). The feeding medium used consists of DMEM/F12 (Invitrogen) supplemented with antibiotics: penicillin (Lonza) and streptomycin (Lonza), with an antifungal agent Fungizone (Invitrogen), with the growth factors EGF (BD) and FGF2 (BD), and with serum substitute supplement B27 (Invitrogen).

The SKPs used are derived from skin specimens and in particular from the foreskins from 3 different donors (8 years old, 10 years old, 22 years old). After a first passage in culture in flasks, the spheres are associated with collagenase and are then put back in culture in the form of individualized cells in the presence of 50% of feeding medium and 50% of conditioned medium (conditioned by the cells themselves).

Evaluation of the Level of Self-Renewal in the Presence or in the Absence of the Rose Dedifferentiated Cells The method used to evaluate the levels of self-renewal is similar to that used during the passages of the cells. The SKPs are first dissociated with collagenase, before being seeded in a proportion of 3000 cells per well (in 96-well plates). The cells are cultured in a mixture containing half conditioned medium and half feeding medium, as described previously. The cells are cultivated at 37° C. (21% of $O_2$-5% $CO_2$) and the treatments are performed in the absence (control) or in the presence of 0.43 mg/ml of the active agent derived from Lancôme rosebush dedifferentiated cells, obtained as described in example 2. After the days of culture, the spheres formed are counted in order to evaluate the self-renewal capacity of these cells after treatment.

The results are given in table I hereinafter.

TABLE I

Mean number of spheres per well, per condition, and per biopsy on D10 (mean of 4 wells)

| Treatment | Donor 1 | Donor 2 | Donor 3 | Mean | SD |
|---|---|---|---|---|---|
| +rose dedifferentiated cells | 88.67 | 55.75 | 183.50 | 109.31 | 54.16 |
| − | 52.50 | 33.50 | 112.25 | 66.09 | 33.55 |

The self-renewal of the dermal stem cells is significantly increased after a treatment with the active agent derived from the rose dedifferentiated cells (+treatment) compared with the control (−treatment).

This study makes it possible to conclude that a treatment with the active agent derived from the rose dedifferentiated cells significantly increases the self-renewal capacities of the dermal stem cells in vitro. Given the importance of the role played by these cells in biological processes such as hair follicle regeneration, in the control of the shape of the hair shaft and in skin repair, this result emphasises the advantage of this ingredient as a technical solution for treating aging of the skin and of the hair.

Example 5

Comparison of the "Pro-Regenerating" Effects of the Rose Dedifferentiated Cells with Those of Another Reference "Anti-Aging" Active Agent on a Model of Reconstructed Skin with Low Regenerative Potential The model of reconstructed skin was prepared as indicated in example 2. The active agent derived from the rose dedifferentiated cells was prepared as indicated in example 2. The model of reconstructed skin was treated in the absence (control-culture medium alone) or in the presence of the active agent derived from the rose dedifferentiated cells in a proportion of 0.43 mg/ml, or of retinol in a proportion of 10 µM, for 12 days.

The histological observations were made as indicated in example 2.

As shown in FIG. 3, in the presence of the active agent derived from rose dedifferentiated plant cells, thickening of the epidermis was observed. Furthermore, the basal layer is more dense, the morphological quality is improved and correct differentiation (stratification of the living layers, a semblance of a granular layer) is observed.

On the other hand, treatment with retinol did not improve the epidermal quality and even appears to inhibit differentiation.

The invention claimed is:

1. A cosmetic composition comprising, as active agent, at least one dedifferentiated plant cell of a plant of the *Rosa* sp. genus, or an extract or a lyophilisate of said cells, said dedifferentiated plant cells being obtained by placing cells of a plant of the *Rosa* sp. genus in culture in a culture medium comprising at least $NH_4NO_3$; $KNO_3$; $CaCl_2.2H_2O$; $MgSO_4$; $KH_2PO_4$; $MnSO_4.4H_2O$; $ZnSO_4.7H_2O$; KI; $Na_2MoO_4.2H_2O$; $CuSO_4.5H_2O$; $FeSO_4.7H_2O$; myo-inositol; nicotinic acid; pyridoxine HCl; thiamine HCl; and sucrose; and optionally kinetin, $Na_2EDTA.2H_2O$, and/or naphthaleneacetic acid, wherein the extract is an aqueous solution obtained by grinding the at least one dedifferentiated plant cell in order to obtain a suspension, and then removing the particles from the suspension.

2. A cosmetic method for caring for aged skin or aged hair, comprising administering, to an individual in need thereof, the composition according to claim 1.

3. The method according to claim 2 for treating and/or preventing an esthetic defect subsequent to a deficiency in the tissue renewal of the skin or of the hair.

4. The method according to claim 2 for preventing and/or reducing and/or treating signs of skin aging.

5. The method according to claim 2, wherein the signs of skin aging are chosen from thinning of the skin, a loss of firmness, a loss of elasticity, a loss of density or a loss of tonicity of the skin, dryness of the skin, an alteration of the surface appearance of the skin, the appearance of a marked microrelief of the skin, the appearance of roughness, the formation and/or presence of fine lines and/or of wrinkles, a modification of the radiance of the skin complexion, a wizened appearance of the skin, a modification of the odor of the skin, sagging of the skin, or withering of the skin.

6. The method according to claim 2 for preventing and/or reducing and/or treating thin, lifeless, brittle, weak hair with no hold, no radiance and/or which is graying.

7. The method according to claim 2 for preventing and/or reducing and/or treating partial or total loss of hair fibers.

8. The method according to claim 2 for preventing and/or reducing and/or treating whitening of the hair.

9. The method according to claim 2 wherein the dedifferentiated plant cells are derived from a leaf, a stem, a flower, a petal, a sepal or a root.

10. The method according to claim 2 wherein the dedifferentiated plant cells are derived from a Lancôme delboip rosebush.

11. The method according to claim 2 wherein the dedifferentiated plant cells, or an extract or a lyophilisate of said cells, are formulated in water or a water-soluble organic solvent, or a mixture thereof.

12. The method according to claim 2 wherein the dedifferentiated plant cells, or an extract or a lyophilisate of said cells, are formulated in the presence of a gelling agent and/or of a $C_4$ to $C_6$ sugar.

13. The method according to claim 2 wherein the dedifferentiated plant cells, or an extract or a lyophilisate of said cells, are formulated in the presence of water, of 1,3-propanediol and/or of xanthan gum.

14. The method according to claim 2 wherein the dedifferentiated plant cells, or an extract or a lyophilisate of said cells, are used in an amount representing from 0.01% to 30% relative to the total weight of the composition containing them.

15. The composition according to claim 1 wherein a concentration of the dedifferentiated plant cell of a plant of the *Rosa* sp. genus, or the extract or the lyophilisate of said cell, in the composition is from 0.01% to 50% by weight of dry matter relative to the total weight of the composition.

16. The composition according to claim 1, wherein the active agent is at least one dedifferentiated plant cell derived from a Lancôme delboip rosebush, or an extract or a lyophilisate of said cell.

17. Dedifferentiated plant cells derived from a Lancôme delboip rosebush, or a lyophilisate of said cells.

18. The dedifferentiated plant cells according to claim 17, wherein they are obtained from plant material derived from whole plants or from plant parts.

19. The dedifferentiated plant cells according to claim 17, which cells are obtained from plant material derived from Lancôme delboip rosebush leaves.

20. The dedifferentiated plant cells according to claim 17, which are obtained by means of a method comprising the following steps:
   a) providing Lancôme delboip rose leaves, or cells derived from said leaves,
   b) cultivating the leaves or the cells provided in step a) in the presence of at least one plant hormone, so as to generate dedifferentiated cells, and
   c) recovering the dedifferentiated cells obtained at the end of step b).

21. The rose dedifferentiated cells belonging to the cell line deposited according to the Treaty of Budapest on Jul. 4, 2012, under the reference 2-6307 with the Deutsche Sammlung von Mikroorganismen and Zellkulturen (DSMZ) [German Collection of Microorganisms and Cell Cultures].

22. The composition according to claim 1, wherein the extract is sterilized.

23. A cosmetic composition comprising, as active agent, at least one dedifferentiated plant cell of a plant of the *Rosa* sp. genus, or an extract or a lyophilisate of said cells, said dedifferentiated plant cells being obtained by placing cells of a plant of the *Rosa* sp. genus in culture in a culture medium comprising at least $NH_4NO_3$; $KNO_3$; $CaCl_2.2H_2O$; $MgSO_4$; $KH_2PO_4$; $MnSO_4.4H_2O$; $ZnSO_4.7H_2O$; KI; $Na_2MoO_4.2H_2O$; $CuSO_4.5H_2O$; $FeSO_4.7H_2O$; myo-inositol; nicotinic acid; pyridoxine HCl; thiamine HCl; and sucrose; and optionally kinetin, $Na_2EDTA.2H_2O$, and/or naphthaleneacetic acid,
   wherein the composition is in the form of a gel, a cream, a foam, a capsule, an emulsion, a tablet, an aerosol composition comprising a pressurized propellant, or an ionic or nonionic vesicular dispersion.

24. The composition according to claim 23, wherein the active agent is at least one dedifferentiated plant cell derived from a Lancôme delboip rosebush, or an extract or a lyophilisate of said cell.

25. A cosmetic method for caring for aged skin or aged hair, comprising administering, to an individual in need thereof, a composition comprising, as active agent, the dedifferentiated plant cells or lyophilisate of claim 17.

26. A cosmetic method for caring for aged skin or aged hair, comprising administering, to an individual in need thereof, the composition according to claim 23.

* * * * *